US007258997B2

(12) United States Patent
Brondyk et al.

(10) Patent No.: US 7,258,997 B2
(45) Date of Patent: Aug. 21, 2007

(54) METHODS OF INCREASING PROTEIN EXPRESSION LEVELS

(75) Inventors: William Brondyk, Mansfield, MA (US); Xuliang Jiang, Braintree, MA (US); Rene Lynn Schweickhardt, Medfield, MA (US)

(73) Assignee: Applied Research Systems Ars Holding N.V., Curacao (AN)

( * ) Notice: Subject to any disclaimer, the term of this patent is extended or adjusted under 35 U.S.C. 154(b) by 84 days.

(21) Appl. No.: 10/496,218

(22) PCT Filed: Nov. 21, 2002

(86) PCT No.: PCT/EP02/13059

§ 371 (c)(1),
(2), (4) Date: Sep. 13, 2004

(87) PCT Pub. No.: WO03/046160

PCT Pub. Date: Jun. 5, 2003

(65) Prior Publication Data

US 2005/0074840 A1    Apr. 7, 2005

(51) Int. Cl.
*C12P 21/00*    (2006.01)
*C07K 1/00*    (2006.01)
*C07K 14/00*    (2006.01)

(52) U.S. Cl. .................. 435/69.1; 435/69.52; 530/350; 530/351; 930/144

(58) Field of Classification Search ...................... None
See application file for complete search history.

(56) References Cited

U.S. PATENT DOCUMENTS

| 5,766,917 | A |   | 6/1998 | Wallach et al. |   |
| 5,776,917 | A | * | 7/1998 | Blank et al. ................ | 514/159 |
| 6,271,346 | B1 |  | 8/2001 | Hauptmann et al. |   |
| 6,989,262 | B2 | * | 1/2006 | Bejanin et al. ............. | 435/226 |

OTHER PUBLICATIONS

UniProtKB Entry: P19438—TNR1A —Tumor Necrosis Factor Receptor Superfamily Member 1A precursor (p55), pp. 1-13.*
Information Hyperlinked Over Proteins—Symbol TNFRSF1A, pp. 1-3.*
Aksentijevich et al., Am J Hum Genet. Epub 6 july 2001; 69:301-314.*
UniProtKB Entry: P19438—TNR1A— Tumor Necrosis Factor Receptor Superfamily Member 1A precursor (p55), pp. 1-13 (Feb. 1, 1991).*
Information Hyperlinked Over Proteins—Symbol TNFRSF1A, pp. 1-3 (last accessed Aug. 7, 2006).*
Aksentijevich, I., et al., "The Tumor-Necrosis-Factor Receptor-Associated Periodic Syndrome: New Mutations in TNFRSF1A, Ancestral Origins, Genotype-Phenotype Studies, and Evidence for Further Genetic Heterogeneity of Periodic Fevers," Am. J. Hum. Genet., vol. 69, pp. 301-314 (2001).

Banner, D., et al., "Crystal Structure of the Soluble Human 55 kd TNF Receptor-Human TNFβ Complex: Implications for TNF Receptor Activation," Cell, vol. 73, pp. 431-445 (May 7, 1993).
Bazzoni, F., et al., "The Tumor Necrosis Factor Ligand and Receptor Families," N. Engl. J. Med., vol. 334, pp. 1717-1725 (1996).
Boder, E., et al., Directed Evolution of Antibody Fragments with Monovalent Femtomolar Antigen-Binding Affinity, Proc. Natl. Acad. Sci. USA, vol. 97, No. 20, pp. 10701-10705 (Sept. 26, 2000).
Boder, E., et al., "Yeast Surface Display for Screening Combinatorial Polypeptide Libraries," Nature Biotechnology, vol. 15, pp. 553-557 (Jun. 1997).
Edgington, S., "Rites of Passage: Moving Biotech Proteins Through the ER," Biotechnology, vol. 10, pp. 1413-1420 (Nov. 1992).
Eur. J. of Biochem., vol. 138, pp. 9-37 (1984).
Eur. J. of Biochem., vol. 152, p. 1 (1985).
Eyles, S., et al., "Multiple Roles of Prolyl Residues in Structure and Folding," J. Mol. Biol., vol. 301, pp. 737-747 (2000).
Gietz, R.D., et al., "Studies on the Transformation of Intact Yeast Cells by the LiAc/SS-DNA/PEG Procedure," Yeast, vol. 11, pp. 355-360 (1995).
Hamilton, K., et al., "Tumour Necrosis Factor-Alpha Blockade : A New Era For Effective Management of Rheumatoid Arthritis," Expert Opin. Pharmacother., vol. 1, No. 5, pp. 1041-1052 (Jul. 2000).
Hermes, J., et al., "A Reliable Method for Random Mutagenesis: the Generation of Mutant Libraries using Spiked Oligodeoxyribonucleotide Primers," Gene, vol. 84, pp. 143-141 (1989).
Hobohm, U., et al., "Enlarged Representative Set of Protein Structures," Protein Science, vol. 3, pp. 522-524 (1994).
Holler, P., et al., "In vitro Evolution of a T Cell Receptor With High Affinity For Peptide/MHC," Proc. Natl. Acad. Sci. USA, vol. 97, No. 10, pp. 5387-5392 (2000).
Jordan, M., et al., "Transfecting Mammalian Cells; Optimization of Critical Parameters Affecting Calcium-Phosphate Precipitate Formation," Nucleic Acids Research, vol. 24, No. 4, pp. 596-601 (1996).
Kam, L., et al., "TNF-Alpha antagonists for the Treatment of Crohn's Diseasse," Expert Opin. Pharmacother., vol. 1, No. 4, pp. 615-622 (May 2000).

(Continued)

*Primary Examiner*—Marianne P. Allen
*Assistant Examiner*—Cherie Woodward
(74) *Attorney, Agent, or Firm*—Howrey LLP

(57) ABSTRACT

The present invention relates to methods of increasing protein expression levels whereby at least one amino acid in a protein amino acid sequence is substituted for the amino acid, proline. Preferably, the substitution occurs within 15 amino acids, more preferably within 10 amino acids and most preferably within 5 amino acids of a cysteine amino acid residue. The present invention not only includes methods for polypeptides with proline substitutions, but also polynucleotides with codon substitutions for which a codon for any amino acid, except proline, is substituted for a codon encoding for proline.

5 Claims, 12 Drawing Sheets

OTHER PUBLICATIONS

Kieke, M. et al., "Selection of Functional T Cell Receptor Mutants From a Yeast Surface-Display Library," Proc. Natl. Acad. Sci. USA, vol. 96, pp. 5651-5656 (May 1999).

Kieke, Michele, et al., "Isolation of Anti-T Cell Receptor scFv Mutants by Yeast Surface Display," Protein Engineering, vol. 10, No. 11, pp. 1303-1310 (1997).

Massague, J., et al., "The Transforming Growth Factor-β Family," Annu. Rev. of Cell Biol., vol. 6, pp. 597-641 (1990).

Naismith, J., et al. "Crystallographic Evidence for Dimerization of Unliganded Tumor Necrosis Factor Receptor," J. of Biol. Chem., vol. 270, No. 22, pp. 13303-13307 (1995).

Naismith, J., et al., "Structures of the Extracellular Domain of the Type I Tumor Necrosis Factor Receptor," Structure, vol. 4, No. 11, pp. 1251-1261.

Robzyk, K., et al., "A Simple and Highly Efficient Procedure for Rescuing Autonomous Plasmids from Yeast," Nucleic Acids Research, vol. 20, No. 14, pp. 3790 (1992).

Schreuder, M., et al., "Immobilizing Proteins on the Surface of Yeast Cells," TIBTECH, vol. 14, pp. 115-120 (1993).

Schreuder, M., et al., "Targeting of a Heterologous Protein to the Cell Wall of *Saccharomyces Cerevisiae*," Yeast, vol. 9, pp. 399-409 (1993).

Shusta, E., et al., "Yeast Polypeptide Fusion Surface Display Levels Predict Thermal Stability and Soluble Secretion Efficiency," J. Mol. Biol., vol. 292, pp. 949-956 (1999).

Suter, B., et al., "Cloning of the cDNA Encoding the Porcine p55 Tumor Necrosis Factor Receptor," Gene, vol. 163, pp. 263-266 (1995).

Telliez, J. et al., "Mutational Analysis and NMR Studies of the Death Domain of the Tumor Necrosis Factor Receptor-1," J. Mol. Biol., vol. 300, pp. 1323-1333 (2000).

Tuite, M., et al., "Improving Secretion of Recombinant Proteins From Yeast and Mammalian Cells: Rational or Empirical Design?" TIBTECH, vol. 12, pp. 432-434 (Nov. 1994).

Wang, Y., et al., "A New Procedure for Constructing Peptides into a Given Cα Chain," Folding & Design, vol. 3, No. 1, pp. 1-10 (1997).

Wittrup, K., "Disulfide Bond Formation and Eukaryotic Secretory Productivity," Curr. Opin. in Biotechnology, vol. 6, pp. 203-208 (1995).

Zhang, X., et al., "Site-directed Mutational Analysis of Human Tumor Necrosis Factor-α Receptor Binding Site and Structure-Functional Relationship," Journal of Biological Chemistry, vol. 267, No. 33, pp. 24069-24075 (1992).

* cited by examiner

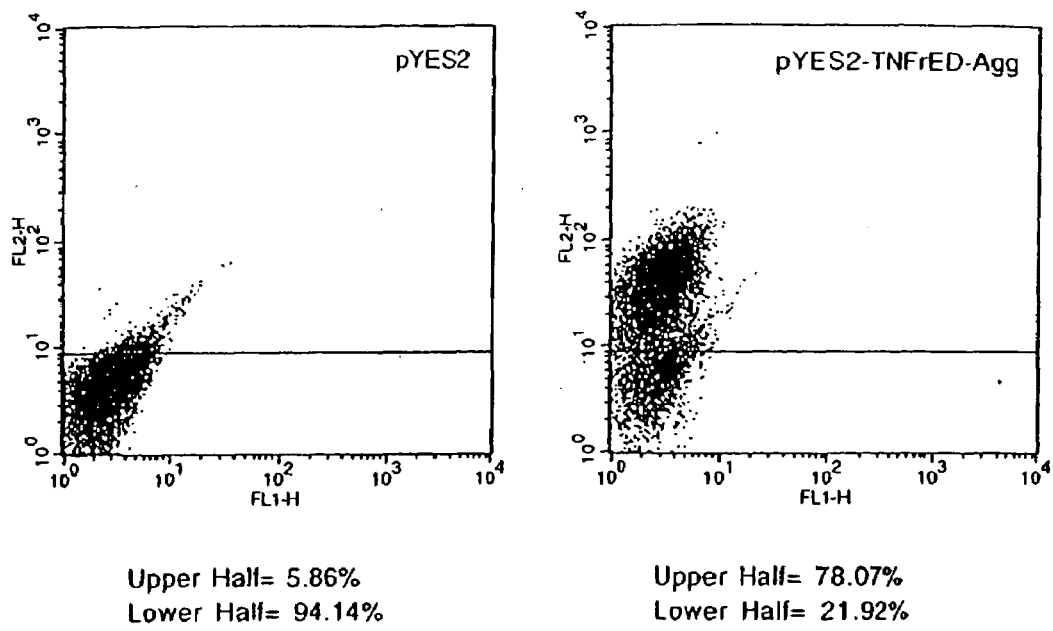

Left Half= 98.58%
Right Half= 1.42%

Left Half= 89.11%
Right Half= 10.89%

Upper Right= 1.71%
R6 region= 0.13%

Upper Right= 13.44%
R6 region= 0.24%

Figure 4

TNFrED sequence

```
        GATAGTGTGTGTCCCCAAGGAAAATATATCCACCCTCAAAATAATTCGATTTGCTGTACC
  1     ---------+---------+---------+---------+---------+---------+    60
        CTATCACACACAGGGGTTCCTTTTATATAGGTGGGAGTTTTATTAAGCTAAACGACATGG
        AspSerValCysProGlnGlyLysTyrIleHisProGlnAsnAsnSerIleCysCysThr
         D   S   V   C   P   Q   G   K   Y   I   H   P   Q   N   N   S   I   C   C   T

AAGTGCCACAAAGGAACCTACTTGTACAATGACTGTCCAGGCCCGGGGCAGGATACGGAC
 61     ---------+---------+---------+---------+---------+---------+   120
        TTCACGGTGTTTCCTTGGATGAACATGTTACTGACAGGTCCGGGCCCCGTCCTATGCCTG
        LysCysHisLysGlyThrTyrLeuTyrAsnAspCysProGlyProGlyGlnAspThrAsp
         K   C   H   K   G   T   Y   L   Y   N   D   C   P   G   P   G   Q   D   T   D

TGCAGGGAGTGTGAGAGCGGaTCCTTCACtGCtTCAGAAAACCACCTCAGACACTGCCTC
121     ---------+---------+---------+---------+---------+---------+   180
        ACGTCCCTCACACTCTCGCCtAGGAAGTGaCGaAGTCTTTTGGTGGAGTCTGTGACGGAG
        CysArgGluCysGluSerGlySerPheThrAlaSerGluAsnHisLeuArgHisCysLeu
         C   R   E   C   E   S   G   S   F   T   A   S   E   N   H   L   R   H   C   L

AGCTGCTCCAAATGCCGAAAGGAAATGGGTCAGGTGGAGATCTCTTCTTGCACAGTcGAC
181     ---------+---------+---------+---------+---------+---------+   240
        TCGACGAGGTTTACGGCTTTCCTTTACCCAGTCCACCTCTAGAGAAGAACGTGTCAgCTG
        SerCysSerLysCysArgLysGluMetGlyGlnValGluIleSerSerCysThrValAsp
         S   C   S   K   C   R   K   E   M   G   Q   V   E   I   S   S   C   T   V   D

CGGGACACCGTGTGTGGCTGCAGGAAGAACCAGTACCGGCATTATTGGAGTGAAAACCTT
241     ---------+---------+---------+---------+---------+---------+   300
        GCCCTGTGGCACACACCGACGTCCTTCTTGGTCATGGCCGTAATAACCTCACTTTTGGAA
        ArgAspThrValCysGlyCysArgLysAsnGlnTyrArgHisTyrTrpSerGluAsnLeu
         R   D   T   V   C   G   C   R   K   N   Q   Y   R   H   Y   W   S   E   N   L

TTCCAGTGCTTCAATTGCAGCCTCTGCCTCAATGGGACCGTGCACCTCTCCTGCCAGGAG
301     ---------+---------+---------+---------+---------+---------+   360
        AAGGTCACGAAGTTAACGTCGGAGACGGAGTTACCCTGGCACGTGGAGAGGACGGTCCTC
        PheGlnCysPheAsnCysSerLeuCysLeuAsnGlyThrValHisLeuSerCysGlnGlu
         F   Q   C   F   N   C   S   L   C   L   N   G   T   V   H   L   S   C   Q   E

AAACAGAACACCGTGTGCACCTGCCATGCAGGTTTCTTTCTAAGAGAAAACGAGTGTGTC
361     ---------+---------+---------+---------+---------+---------+   420
        TTTGTCTTGTGGCACACGTGGACGGTACGTCCAAAGAAAGATTCTCTTTTGCTCACACAG
        LysGlnAsnThrValCysThrCysHisAlaGlyPhePheLeuArgGluAsnGluCysVal
         K   Q   N   T   V   C   T   C   H   A   G   F   F   L   R   E   N   E   C   V
```

Figure 4 Continued

```
      TCCTGTAGTAACTGTAAGAAAAGCCTGGAGTGCACGAAGTTGTGCCTACCCCAGATTGAG
421   ---------+---------+---------+---------+---------+---------+   480
      AGGACATCATTGACATTCTTTTCGGACCTCACGTGCTTCAACACGGATGGGGTCTAACTC
      SerCysSerAsnCysLysLysSerLeuGluCysThrLysLeuCysLeuProGlnIleGlu
       S   C   S   N   C   K   K   S   L   E   C   T   K   L   C   L   P   Q   I   E

AATTGA
481   ------   486
      TTAACT
      AsnEnd
       N   *
```

METHODS OF INCREASING PROTEIN EXPRESSION LEVELS

BACKGROUND OF THE INVENTION

1. Field of the Invention

The present invention relates to methods of increasing protein expression levels whereby at least one amino acid in a polypeptide amino acid sequence is substituted for the amino acid, proline.

2. Background

The ability to obtain a high level of expression of secreted recombinant proteins in yeast and mammalian cells is often found to be protein dependent. Efforts in maximizing recombinant protein expression are often focused on increasing the levels of the mRNA of the recombinant gene. However, the rate-limiting step in the expression of certain proteins is not the level of mRNA but rather is due to inefficiencies in the folding, addition of post-translational modifications and secretion of the recombinant proteins.

Combining random mutagenesis with the display of proteins on the surface of yeast is a powerful technique to identify proteins with altered properties. In this technique, mutant proteins are displayed on the cell surface and screened for either higher-affinity binding or increased expression levels of the displayed protein by FACS (fluorescence activated cell sorting). Display of mutant libraries on the yeast cell surface has been used to identify mutants of both single-chain antibodies and single-chain T-cell receptors that have a higher affinity for antigen or peptide/MHC, respectively. The yeast surface display method has also been used to improve the level of expression of a single-chain T-cell receptor.

There remains a need in the art for identifying structural characteristics or features of proteins which permit high expression of recombinant proteins, particularly eukaryotic proteins, whose expression may be limited due to inefficiencies in folding, addition of post-translational modifications and/or secretion of proteins.

SUMMARY OF THE INVENTION

The present invention relates to methods of increasing protein expression levels whereby at least one amino acid in a protein amino acid sequence is substituted for the amino acid, proline. Preferably, the substitution occurs within 15 amino acids, more preferably within 10 amino acids and most preferably within 5 amino acids of a cysteine amino acid residue. The present invention not only includes methods for polypeptides with proline substitutions, but also polynucleotides with codon substitutions for which a codon for any amino acid, except proline, is substituted for a codon encoding for proline. Specifically, the codons encoding proline are CCU, CCC, CCA and CCG for RNA and CCT, CCC, CCA, and CCG for DNA.

Any protein of interest can be included in the invention, provided that it can be expressed from a recombinant DNA molecule in a suitable host cell and remain functionally active. Preferably, the protein is one whose expression is limited by constraints on conformational folding. More preferably, the protein will contain one or more cysteine amino acid residues and may require the formation of correct disulfide bonds, resulting in proper conformational folding of the tertiary structure of the polypeptide.

The present invention solves, in part, the continuing need in the art for means to improve the efficiency of expression of recombinant proteins in mammalian and other host cells.

The invention provides methods that overcome the problem of inefficient folding of polypeptides, which limits the expression of certain heterologous polypeptides, and provides for higher levels of expression of such polypeptides.

BRIEF DESCRIPTION OF THE FIGURES

FIG. 1A represents a diagrammatic representation of a flow cytometric analysis of yeast cells stained with a polyclonal antibody directed against TNFrED and R-phycoerythrin-conjugated donkey anti-goat IgG. Yeast cells contained either the pYES2 plasmid (left panel) or the pYES2-TNFrED-Agg plasmid (right panel).

FIG. 4 presents amino acids 12-172 and the encoding polynucleotide sequence of TNFrED.

DETAILED DESCRIPTION OF THE INVENTION

The present invention is based on the unexpected finding that the substitution of one or more amino acids for the amino acid proline in the amino acid sequence of a polypeptide results in higher levels of expression of that protein. While not wishing to be bound by theory, evidence supports the suggestion that the biochemical mechanism allowing higher levels of expression relates to the promotion of proper conformational folding of a protein.

Through screening of mutant clones of the extracellular domain of the receptor for Tissue Necrosis Factor (TNFrED) with the yeast display system we were able to identify mutations of TNFrED that conferred a higher expression level in yeast when compared to wild-type TNFrED. One clone contained the S76P mutation and the other clone contained the H23P and S46I mutations. These mutations did not change the affinity of TNFrED for TNF-α. Expression of these mutants in mammalian cells generated similar findings, strongly suggesting that the mechanism through which the mutations increase expression is conserved between yeast and mammalian cells. Examination of the mutations individually or in combination revealed that either proline change increased the expression of TNFrED whereas the S46I mutation had no effect on expression.

Figure 3:
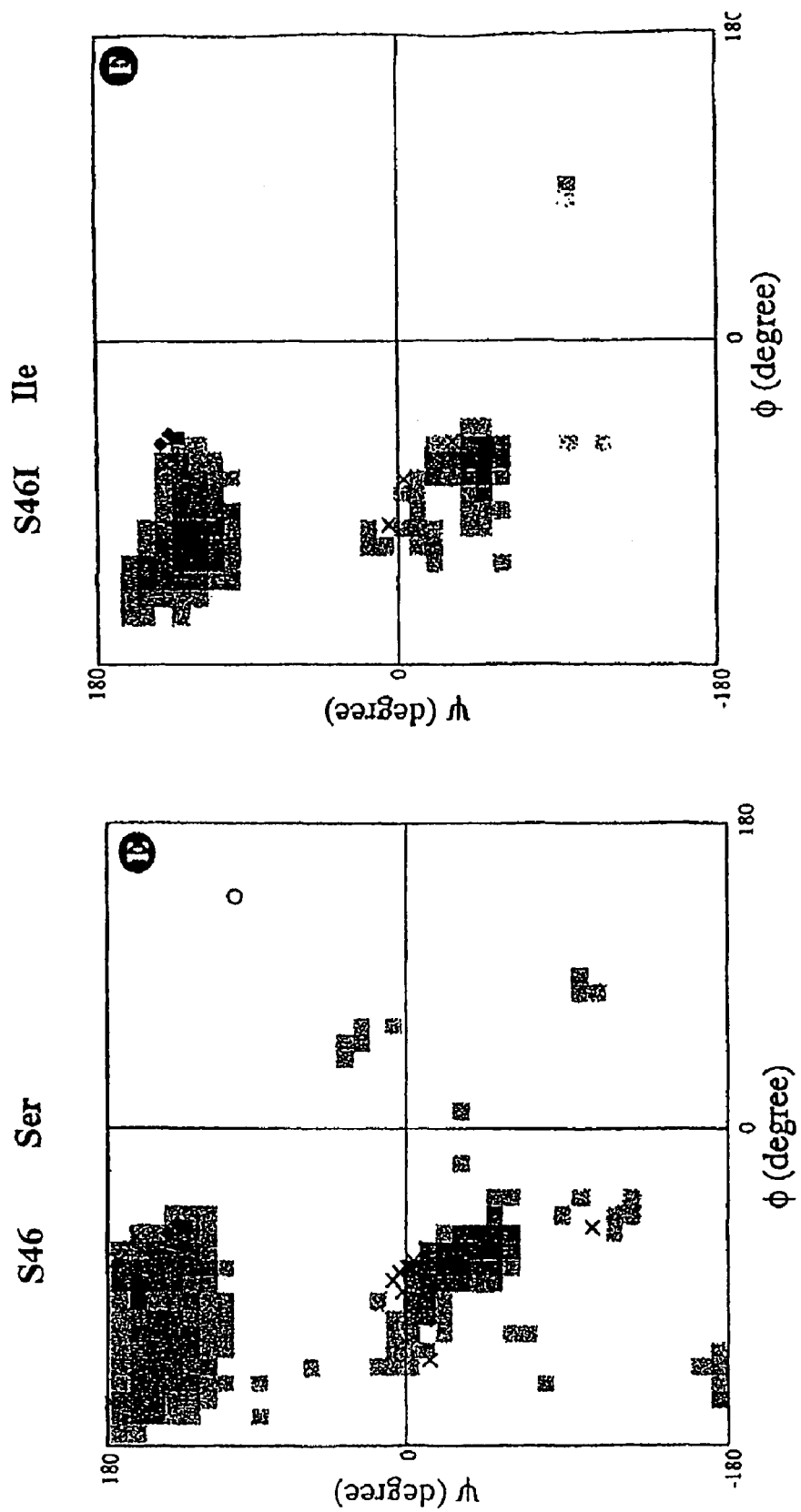
FIG. 3 is a diagrammatic representation of the φ-ψ plot of the substituted residues in the mutant clones 6 and 11 and the corresponding residues found in wild-type TNFrED wherein the shaded regions are the favorable conformations obtained from an analysis of 136 non-homologous protein structures at a resolution of 1.8 Å or higher. The darker the color, the higher the frequency of the φ-ψ angles of the residues, and hence the more favored conformation. The φ-ψ angles of the corresponding residue in the TNFrED crystal structures are shown in red squares (1 ncf.pdb, TNFrED dimer structure, 1.85 Å resolution), red diamonds (1 ext.pdb, TNFrED dimer structure, 2.85 Å resolution), and red triangles (1tnr.pdb, TNF/TNFrED complex structure, 2.85 Å resolution). The representative high-resolution dataset was used to generate the green symbols and these symbols represent the φ-ψ angles of the substituted residue in the same tri- (green 'x's) or tetra-(green circles) amino acid context as that found in wild-type TNFrED or the mutant clones (see also Table 4). (A). Ser76. (B) Pro76. (C). His23. (D) Pro23. (E). Ser46. (F). Ile46.
Figure 3B:
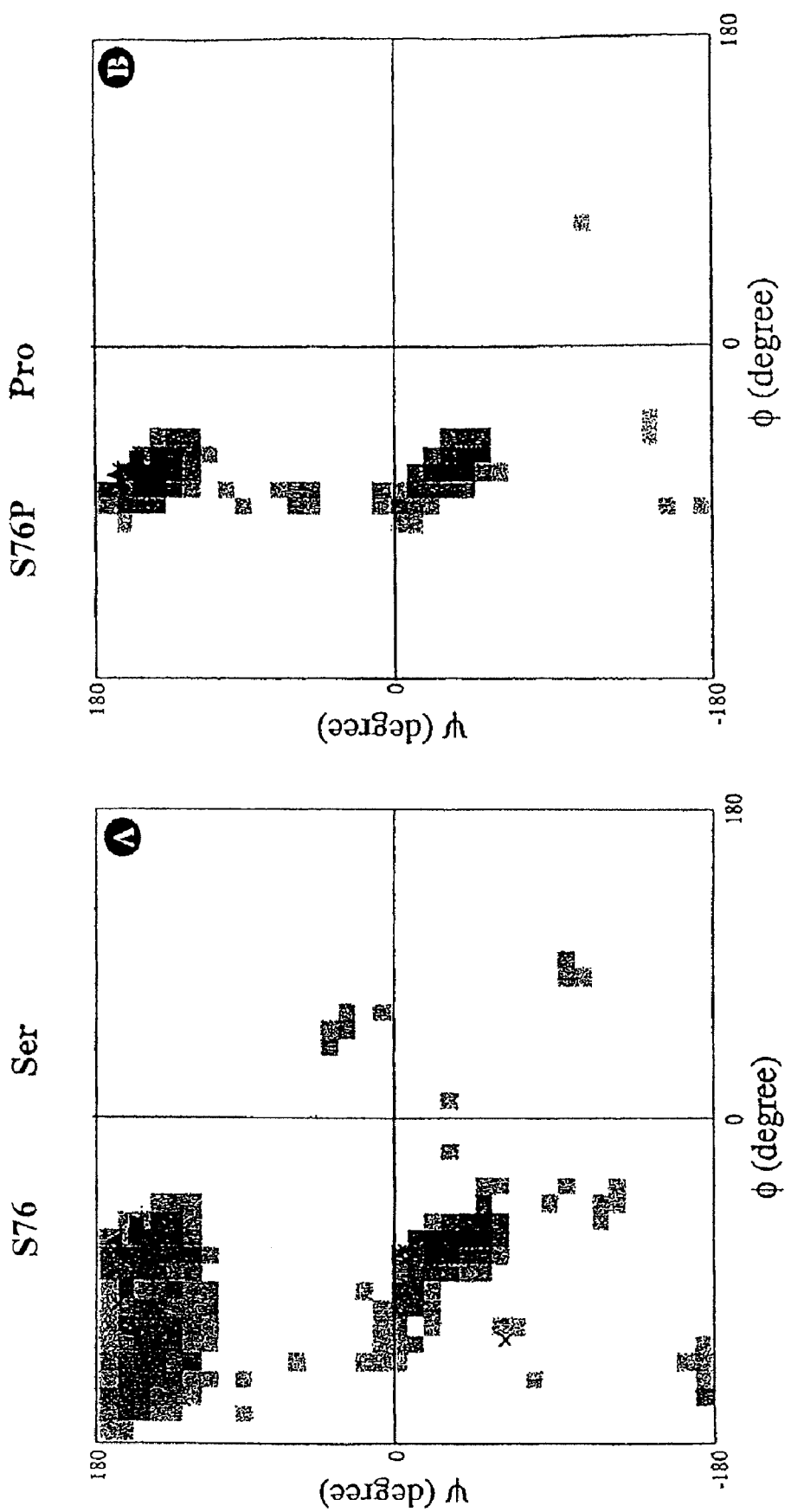
Figure 3C:
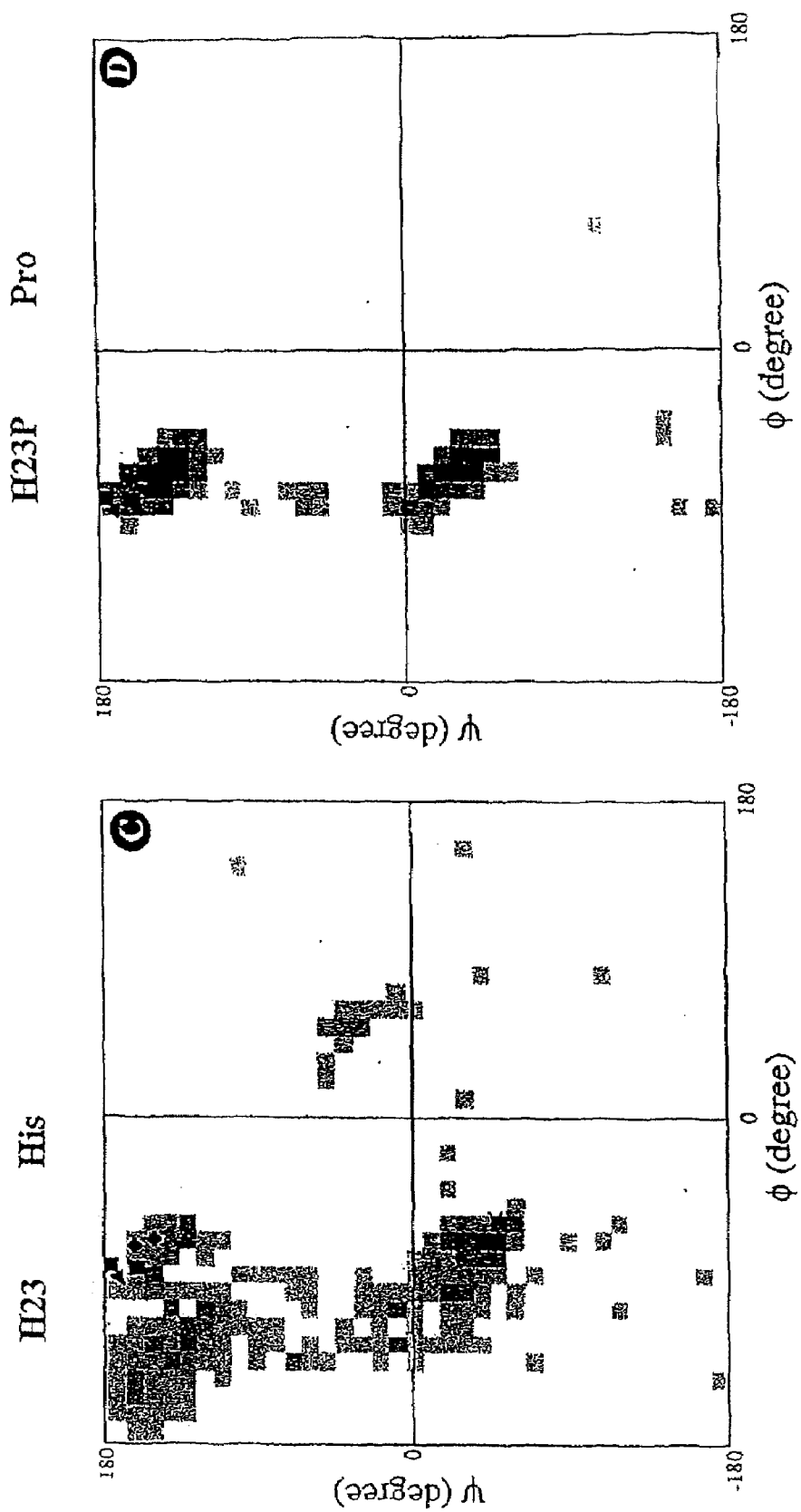

In each mutant clone, we showed that the residue responsible for the higher protein expression levels is a proline substitution next to a cysteine involved in a disulfide bond. In proline the nitrogen atom is part of a rigid ring and no rotation of the ring N—C bond is possible. Thus the choices of φ-ψ angles are fewer in the proline substitutions than the histidine or serine residues found in the wild-type TNFrED (shaded areas in FIG. 3). Moreover, the φ-ψ angles of the histidine or serine residue found in the crystal structures of TNFrED are located in the more favored regions of the φ-ψ plot of a proline residue. These results indicate that proline is the preferred residue at position 23 or 76 in terms of the main-chain conformation. This phenomenon is more evident in the uncomplexed structure of TNFrED with the highest resolution (pdb code: 1ext; see the red filled squares in FIG. 3). Therefore, the mutations have no advantage in the complexed form compared to the uncomplexed form, which is in agreement with our observation that the mutants do not affect the affinity of TNFrED for ligand. To test if there is any change of the favorable status of a proline for the given φ-ψ angles when the adjacent one or two amino acids are also considered, we searched the representative PDB dataset for the same sequences in the mutated form and the wild-type form. There are more cases of mutated sequences than the wild-type sequences (see Table 3 and also the green 'x's in FIG. 3). These results further emphasize that proline is the preferred residue at position 23 or 76, both in terms of the main-chain conformation for that particular residue and also for when the surrounding residues and structure environment are taken into consideration. The S46I mutation is a different situation. It results in a narrower region of φ-ψ angles but deviates away from the preferred φ-ψ. angle region to a slightly less preferred region (FIG. 3). Thus, there appears to be no advantage of the S46I mutation in term of φ-ψ. preference at that position. This is consistent with our experimental observation that the presence of the S46I mutation alone does not significantly alter the expression level of TNFrED. Taking all the data together, we conclude that introduction of the proline residues assists the local sequence of each mutant to adopt the conformations seen in crystal structures of TNFrED thereby fixing neighboring cysteine residues into the correct orientation. We proposed that proper orientation of the cysteine in turn facilitates formation of the correct disulfide bond and results in a higher yield of correctly folded molecules. Our finding that these proline substitutions increase the expression level of TNFrED is consistent with this proposal. Furthermore, proline substitutions can be extended to other proteins where the formation of disulfide bonds is thought to be a limiting factor in expression.

The present invention relates to methods of increasing protein expression levels whereby at least one amino acid in a protein amino acid sequence is substituted for the amino acid, proline. Preferably, the substitution in these proline-substituted polypeptides occurs within 15 amino acids, more preferably within 10 amino acids and most preferably within 5 amino acids of a cysteine amino acid residue. The present invention not only includes methods for polypeptides with proline substitutions, but also polynucleotides with codon substitutions for which a codon for any amino acid, except proline, is substituted for a codon encoding for proline. Specifically, the codons encoding proline are CCU, CCC, CCA, CCG for RNA and CCT, CCC, CCA, CCG for DNA (see Table 1).

I. Definitions:

In general, the following words or phrases have the indicated definition when used in the description, examples and claims.

"Protein" shall mean any polypeptide comprised of amino acids and having a unique amino acid sequence. The term "protein" may be used interchangeably herein with the term "polypeptide".

"Substitution" shall mean the introduction of an amino acid, either by replacement of an existing amino acid residue or by insertion of an additional residue. In the present invention, the replacement or inserted amino acid is proline.

"Increased Expression" shall mean higher or greater expression levels of protein when comparing the expression levels of a protein with its original amino acid sequence with the expression levels of the same protein with one or more proline substitutions.

"Amino Acid" shall mean an amino acid residue contained in the group consisting of the 20 naturally occurring amino acids. In the present application, amino acid names are used as defined by the Protein DataBank (PDB) (www-.pdb.org), which is based on the IUPAC nomenclature (IUPAC Nomenclature and Symbolism for Amino Acids and Peptides (residue names), *Eur. J. Biochem.*, 138, 9-37 (1984) together with their corrections in *Eur. J. Biochem.*, 152, 1 (1985); i.e. alanine (Ala or A), cysteine (Cys or C), aspartic acid (Asp or D), glutamic acid (GLU or E), phenylalanine (Phe or F), glycine (Gly or G), histidine (His or H), isoleucine (Ile or I), lysine (Lys or K), leucine (Leu or L), methionine (Met or M), asparagine (Asn or S), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

"Positioned Within" shall mean being positioned proximal to a particular reference amino acid in an amino acid sequence, in either the 3' or 5' direction.

"Codon" shall mean a triplet of nucleotides coding for a single amino acid. (see Table 1)

"Polynucleotide" shall mean a single stranded molecule of DNA or RNA.

The terminology used for identifying amino acid positions/substitutions is illustrated as follows: H23P indicates that position number 23 in the linear sequence of amino acids shown in FIG. 4 and SEQ ID NO: 1 is occupied by a histidine residue and that it has been substituted with a proline residue. Unless otherwise indicated, the numbering of amino acid residues made herein is made relative to the amino acid sequence shown in FIG. 4 and SEQ ID NO: 1

(depicting residues 12-172 of hTNFrED). Multiple substitutions are indicated with a "+", e.g., H23P+S46I means an amino acid sequence which comprises substitution of the histidine residue in position 23 by a proline residue and substitution of the serine residue in position 46 by a isoleucine residue.

TABLE 1

The Genetic Code (RNA to Amino Acids)*

| First Position (5' end) | Second Position | | | | Third Position (3' end) |
|---|---|---|---|---|---|
| | U | C | A | G | |
| U | Phe | Ser | Tyr | Cys | U |
| | Phe | Ser | Tyr | Cys | C |
| | Leu | Ser | Stop (och) | Stop | A |
| | Leu | Ser | Stop (amb) | Trp | G |
| C | Leu | Pro | His | Arg | U |
| | Leu | Pro | His | Arg | C |
| | Leu | Pro | Gln | Arg | A |
| | Leu (Met) | Pro | Gln | Arg | G |
| A | Ile | Thr | Asn | Ser | U |
| | Ile | Thr | Asn | Ser | C |
| | Ile | Thr | Lys | Arg | A |
| | Met (start) | Thr | Lys | Arg | G |
| G | Val | Ala | Asp | Gly | U |
| | Val | Ala | Asp | Gly | C |
| | Val | Ala | Glu | Gly | A |
| | Val (Met | Ala | Glu | Gly | G |

Methods for Generating an Expression System for Proline Substituted Polypeptides:

The proline substituted polypeptides of the present invention may be produced by any suitable method known in the art. These methods include the construction of nucleotide sequences encoding the respective proline substituted polypeptides and expressing the amino acid sequence in a suitable transfected host. Proline substituted polypeptides of the present invention may also be produced by chemical synthesis or by a combination of chemical synthesis and recombinant DNA technology.

Proline substituted polypeptides of the invention may be constructed by isolating or synthesizing a nucleotide sequence encoding the parent. The nucleotide sequence is then changed so as to effect the substitution of the relevant amino acid residue(s). The nucleotide sequence can be modified by site directed mutagenesis as in the Examples of the present specification. In the alternative, the nucleotide sequence may be prepared by chemical synthesis, wherein oligonucleotides are designed based on the specific amino acid sequence of the proline substituted polypeptides.

The nucleotide sequence encoding the proline substituted polypeptide is inserted into a recombinant vector and operably linked to control sequences necessary for expression of the polypeptide in the desired transfected host cell. One of skill in the art may make a selection among these vectors, expression control sequences and hosts without undue experimentation.

The recombinant vector may be an autonomously replicating vector, i.e. a vector which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector in which the nucleotide sequence encoding the polypeptide of the invention is operably linked to additional segments required for transcription of the nucleotide sequence. The vector is typically derived from plasmid or viral DNA. A number of suitable expression vectors for expression in the host cells mentioned herein are commercially available or described in the literature The recombinant vector may further comprise a DNA sequence enabling the vector to replicate in the host cell in question. An example of such a sequence, (when the host cell is a mammalian cell) is the SV40 origin of replication.

The vector may also comprise a selectable marker, e.g. a gene whose product complements a defect in the host cell, such as the gene coding for dihydrofolate reductase (DHFR) or one which confers resistance to a drug, e.g. ampicillin, kanamycin, tetracycline chloramphenicol, neomycin, hygromycin or methotrexate.

The vector may also comprise an amplifiable gene, such as DHFR, such that cells having multiple copies of the amplifiable gene and flanking sequences, including the proline substituted polypeptide DNA, can be selected for on appropriate media.

The term "control sequences" is defined herein to include all components which are necessary or advantageous for the expression of the polypeptide of the invention. Examples of suitable control sequences for directing transcription in mammalian cells include the early and late promoters of SV40 and adenovirus, e.g. the adenovirus 2 major late promoter, the MT-1 (metallothionein gene) promoter and the human cytomegalovirus immediate-early gene promoter (CMV).

The nucleotide sequences of the invention encoding the proline substituted polypeptides, whether prepared by site-directed mutagenesis, synthesis, PCR or other methods, may optionally also include a nucleotide sequence that encodes a signal peptide. The signal peptide is present when the polypeptide is to be secreted from the cells in which it is expressed. Such signal peptide, if present, should be one recognized by the cell chosen for expression of the polypeptide. The signal peptide may be homologous (e.g. be that normally associated with the parent polypeptide) or heterologous (i.e. originating from another source than parent polypeptide) to the polypeptide or may be homologous or heterologous to the host cell, i.e. be a signal peptide normally expressed from the host cell or one which is not normally expressed from the host cell.

Any suitable host may be used to produce the proline substituted polypeptide of the invention, including bacteria, fungi (including yeasts), plant, insect, mammal, or other appropriate animal cells or cell lines, as well as transgenic animals or plants. Examples of suitable mammalian host cells include Chinese hamster ovary (CHO) cell lines, (e.g. CHO-KL; ATCC CCL-61), Green Monkey cell lines (COS) (e.g. COS 1 (ATCC CRL-1650), COS 7 (ATCC CRL-1651)); mouse cells (e.g. NSIO), Baby Hamster Kidney (BI-EK) cell lines (e.g. ATCC CRL-1632 or ATCC CCL-10), and human cells (e.g. BEK 293 (ATCC CRL-1573)), as well as plant cells in tissue culture. Additional suitable cell lines are known in the art and available from public depositories such as the American Type Culture Collection, USA. Methods for introducing exogeneous DNA into mammalian host cells include calcium phosphate-mediated transfection, electroporation, DEAE-dextran mediated transfection, liposome-mediated transfection and viral vectors.

Cells are cultivated in a nutrient medium suitable for production of the proline substituted polypeptide using methods known in the art. For example, the cell may be cultivated by shake flask cultivation, small-scale or largescale fermentation (including continuous, batch, fed-batch, or solid state fermentations) in laboratory or industrial fermenters performed in a suitable medium and under conditions allowing the proline substituted polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g. in catalogues of the American Type Culture Collection). If the proline substituted polypeptide is secreted into the nutrient medium, it can be recovered directly from the medium. If the proline substituted polypeptide is not secreted, it can be recovered from cell lysates.

The resulting proline substituted polypeptide may be recovered by methods known in the art. For example, it may be recovered from the nutrient medium by conventional procedures including, but not limited to, centrifugation, filtration, extraction, spray drying, evaporation, or precipitation.

The proline substituted polypeptides may be purified by a variety of procedures known in the art including, but not limited to, chromatography (e.g. ion exchange, affinity, hydrophobic, chromatofocusing, and size exclusion), electrophoretic procedures (e.g. preparative isoelectric focusing), differential solubility (e.g. ammonium sulfate precipitation), SDS-PAGE, or extraction.

Pharmaceutical Composition of the Invention and its Use

In one aspect, the proline substituted polypeptide or the pharmaceutical composition according to the invention is used for the manufacture of a medicament for treatment of diseases, disorders or conditions.

In another aspect the proline substituted polypeptide or the pharmaceutical composition according to the invention is used in a method of treating a mammal, in particular a human, comprising administering to the mammal in need thereof such proline substituted polypeptide or pharmaceutical composition thereof.

It will be apparent to those of skill in the art that an effective amount of a conjugate, preparation or composition of the invention depends, inter alia, upon the disease, the dose, the administration schedule, whether the polypeptide or conjugate or composition is administered alone or in conjunction with other therapeutic agents, the serum half-life of the compositions, and the general health of the patient. Typically, an effective dose of the preparation or composition of the invention is sufficient to ensure a therapeutic effect.

The proline substituted polypeptide produced by the methods of the invention is normally administered in a composition including one or more pharmaceutically acceptable carriers or excipients. "Pharmaceutically acceptable" means a carrier or excipient that does not cause any untoward effects in patients to whom it is administered. Such pharmaceutically acceptable carriers and excipients are well known in the art, and the polypeptide or conjugate of the invention can be formulated into pharmaceutical compositions by well-known methods (see e.g. Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)). Pharmaceutically acceptable excipients that may be used in compositions comprising the polypeptide or conjugate of the invention include, for example, buffering agents, stabilizing agents, preservatives, isotonifiers, nonionic surfactants or detergents ("wetting agents"), antioxidants, bulking agents or fillers, chelating agents and cosolvents.

The pharmaceutical composition of the proline substituted polypeptide of the invention may be formulated in a variety of forms, including liquids, e.g. ready-to-use solutions or suspensions, gels, lyophilized, or any other suitable form, e.g. powder or crystals suitable for preparing a solution. The preferred form will depend upon the particular indication being treated and will be apparent to one of skill in the art.

The pharmaceutical composition containing the proline substituted polypeptide of the invention may be administered intravenously, intramuscularly, intraperitoneally, intradermally, subcutaneously, sublingualy, buccally, intranasally, transdermally, by inhalation, or in any other acceptable manner, e.g. using PowderJect@ or ProLease(D technology or a pen injection system. The preferred mode of administration will depend upon the particular indication being treated and will be apparent to one of skill in the art. In particular, it is advantageous that the composition be administered subcutaneously, since this allows the patient to conduct the self-administration.

The pharmaceutical composition of the invention may be administered in con-junction with other therapeutic agents. These agents may be incorporated as part of the same pharmaceutical composition or may be administered separately from the polypeptide or conjugate of the invention, either concurrently or in accordance with any other acceptable treatment schedule. In addition, the polypeptide, conjugate or pharmaceutical composition of the invention may be used as an adjunct to other therapies.

Exemplification: Enhanced Expression of Tissue Necrosis Factor (TNF)

The extracellular domain of the p55 TNF receptor (TNFrED) was randomly mutated and libraries of TNFrED mutants were displayed on the surface of yeast cells. Two mutant TNFrED clones were identified by fluorescence-activated cell sorting (FACS) that expressed two- to five-fold higher in yeast compared to wild-type TNFrED. In one mutant clone there was a Ser to Pro change at position 76 and in the other mutant clone there was a His to Pro change at position 23 and a Ser to Ile change at position 46. The presence of either the S76P or H23P mutation resulted in higher expression levels of TNFrED in HEK293-EBNA cells whereas the S46I mutation had no effect on expression. These substituted residues did not have an effect on the affinity for TNF-α. Examination and analysis of the substituted residues in the crystal structures of TNFrED indicates that the introduction of proline residues likely assists the local sequence of the mutants to adopt favorable conformations that fix the neighboring cysteine residues into the correct orientation for proper disulfide bond formation. This facilitation of the formation of selected disulfide bonds then results in a higher yield of correctly folded molecules in both yeast and mammalian cells.

EXAMPLE 1

Expression of Functional TNFrED on the Surface of *S. cerevisae*

Figure 1B:
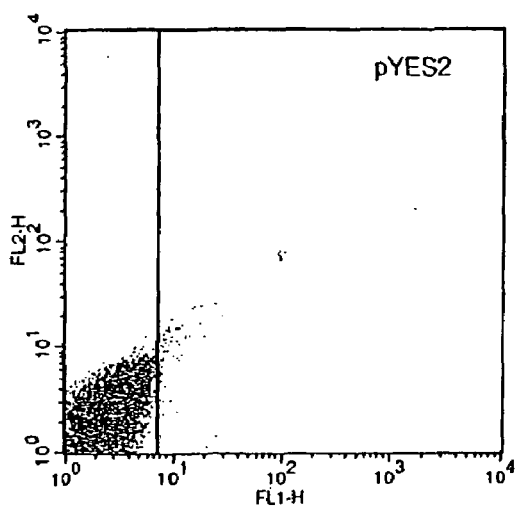
FIG. 1B is a diagrammatic representation of a flow cytometric analysis of yeast cells stained with biotinylated hTNF-α and FITC-labeled avidin. Yeast contained either the pYES2 plasmid (left panel) or the pYES2-TNFrED-Agg plasmid (right panel).
Figure 1B:
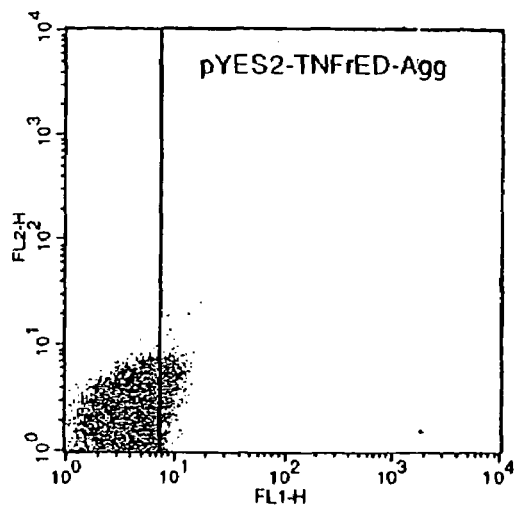

The extracellular domain of the p55 TNF receptor (TNFrED) was fused to the C-terminal portion of α-agglutinin and expressed in the *S cerevisae* strain BJ2168 (a, prc1-407, prb1-1122, pep4-3, leu2, trp1, ura3-52) using the pYES2 vector. The C-terminal portion of α-agglutinin is tightly anchored in the cell wall and serves as a scaffold to present TNFrED on the cell surface. To facilitate the transport of the TNFrED-agglutinin fusion protein into the secretory pathway, the signal sequence of TNF receptor was replaced with the yeast invertase signal sequence. The TNFrED-agglutinin fusion gene was under the regulation of the inducible GAL1 promoter. Switching the carbon source of the yeast culture from glucose to galactose resulted in induction of the GAL1 promoter and expression of TNRrED-agglutinin. In a flow cytometric analysis with polyclonal antibodies directed against TNFrED we found that in an induced culture approximately 70% of the yeast expressed TNFrED-agglutinin on the cell surface (FIG. 1A). To determine whether TNFrED on the yeast cell surface was folded correctly and could bind TNF-α we performed a flow cytometric analysis using biotinylated TNF-α as a probe and FITC-labeled avidin as the detection reagent. Yeast expressing the TNFrED-agglutinin fusion gene bound more biotinylated TNF-α than did yeast containing the pYES2 vector (FIG. 1B). Adding excess unlabeled TNF-α (data not shown) reversed the shift in the histogram seen with the yeast expressing the TNFrED-agglutinin fusion gene.

EXAMPLE 2

Selection of Mutant TNFrED Clones with Enhanced Biotinylated-TNF-α Binding

Figure 1C:
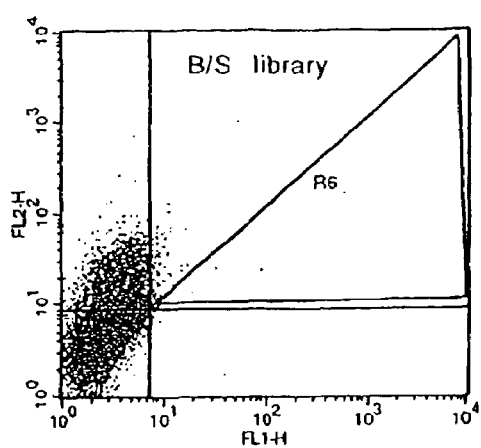
FIG. 1C is a diagrammatic representation of a two-color flow cytometric analysis of yeast cells that have been stained with biotinylated hTNF-α and FITC-labeled avidin and a polyclonal antibody directed against TNFrED and R-phycoerthrin-conjugated donkey anti-goat IgG. Yeast were transformed with a mutant library (left panel) or with the same library after three rounds of sorting (right panel).
Figure 1C:
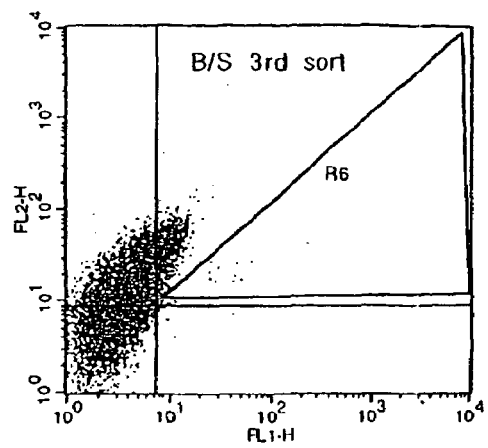
Figure 1D:
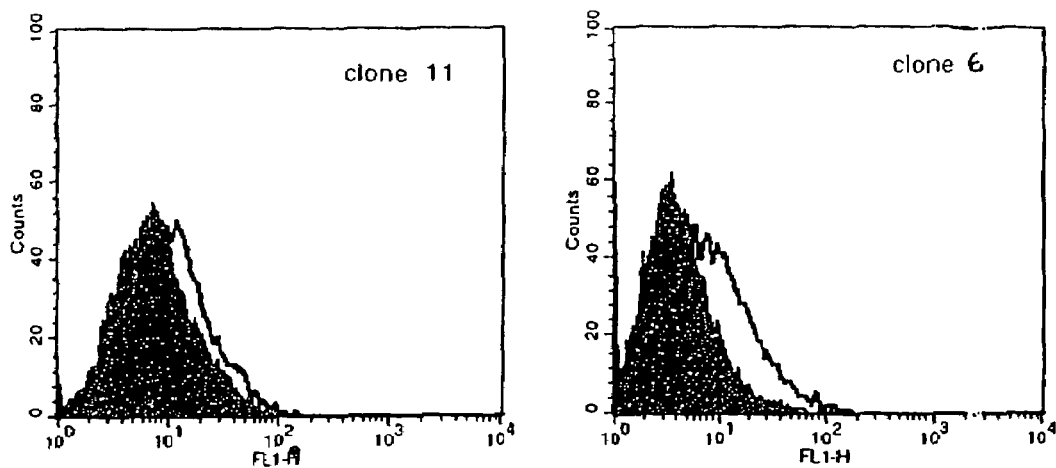
FIG. 1D is a diagrammatic representation of a flow cytometric analysis of yeast cells stained with biotinylated hTNF-α and FITC-labeled avidin. In the left panel the shaded histogram represents the yeast expressing wild-type TNFrED whereas the unshaded histogram represents clone 11. In the right panel the shaded histogram represents the yeast expressing wild-type TNFrED whereas the unshaded histogram represents clone 6.

A modification of the mutagenesis approach previously described (Hermes, J. D., Parekh, S. M., Blacklow, S. C., Koster, H. & Knowles, J. R. A reliable method for random mutagenesis: the generation of mutant libraries using spiked oligodeoxyribonucleotide primers. *Gene* 84, 143-151 (1989)) was used to generate random mutant libraries. In this approach mutant oligonucleotides are produced by spiking a predetermined level of the "wrong" nucleotides at each position. The level of contamination of the wrong nucleotides was adjusted to generate either an average of two or three random point mutations per oligonucleotide. Each mutant library covered between 40 to 105 base pairs of TNFrED. Ten random clones from each library were sequenced. The type and the position of mutations were random and the regions were found to contain the anticipated average number of mutations. Approximately 40-50% of the clones contained either a small deletion or insertion, which results in the expression of a truncated TNFrED. Presumably these deletions or insertions resulted from errors incorporated during the oligonucleotide synthesis process. The size of each library was between $0.5 \times 10^6$ and $10 \times 10^6$ independent mutant clones. Each library was transformed into the strain BJ2168 and approximately $1 \times 10^6$ independent transformants were selected for binding to both biotinylated-TNF-α and polyclonal antibodies directed against the TNFrED. The window of the two-dimensional fluorescence histogram that was chosen to select for the subpopulation of yeast expressing active TNFrED is shown in FIG. 1C. The selected subpopulation of yeast was grown and reselected with two-color sorting. After several rounds of two-color sorting the population of yeast in the selected window was enriched (FIG. 1C). Following three to four rounds of cell sorting, individual clones were analyzed by examining binding of biotinylated-TNF-α to the TNFrED on the cell surface. A majority of the clones analyzed from each sorted library appeared to bind higher levels of biotinylated-TNF-α. The mutant TNFrED plasmid was recovered from each yeast clone and re-transformed into the BJ2168 strain and then analyzed by flow cytometry for binding of biotinylated-TNFα. The vast majority of yeast clones were false positives as the recovered plasmids did not confer higher levels of biotinylated-TNF-α binding. When false positive yeast clones were analyzed in the absence of biotinylated TNF-α and avidin-FITC, they were found to be shifted as compared to the parental BJ2168 strain. These false positive yeast clones are approximately 30% larger in size compared to the parental BJ2168, which is presumably what gives rise to the shift in the baseline absorbance. However, two mutant clones, 6 and 11, from different libraries were identified that when transformed into the BJ2138 strain conferred higher levels of binding of biotinylated TNF and therefore are true positives (FIG. 1D).

EXAMPLE 3

Characterization of Mutant Clones 6 and 11

The TNFrED coding region in mutant clones 6 and 11 was sequenced and, as anticipated, the mutations for each clone were only found in the sequence region mutated for that specific library. In mutant clone 11 there was a point mutation that results in Ser to Pro change at position 76 and in mutant clone 6 there were two point mutations that result in an His to Pro change at position 23 and a Ser to Ile change at position 46.

To determine whether the mutations increase binding of biotinylated TNF through increased expression of TNFrED or by increasing the affinity of TNFrED for TNF, we performed a saturation binding experiment on yeast expressing either mutant clone 6 or 11. Analysis of saturation binding experiments (FIG. 2) indicated that yeast expressing either mutant clone 6 or 11 express higher levels of functional TNFrED than wild-type TNFrED and that the presence of these mutations does not affect the affinity of TNFrED for TNF-α. The approximate number of receptors/cell for yeast expressing mutant clone 6, mutant clone 11 and wild-type TNFrED was 3930, 1490, 740, respectively.

EXAMPLE 4

Expression of Mutated TNFrEDs in Mammalian Cells

Figure 2A:
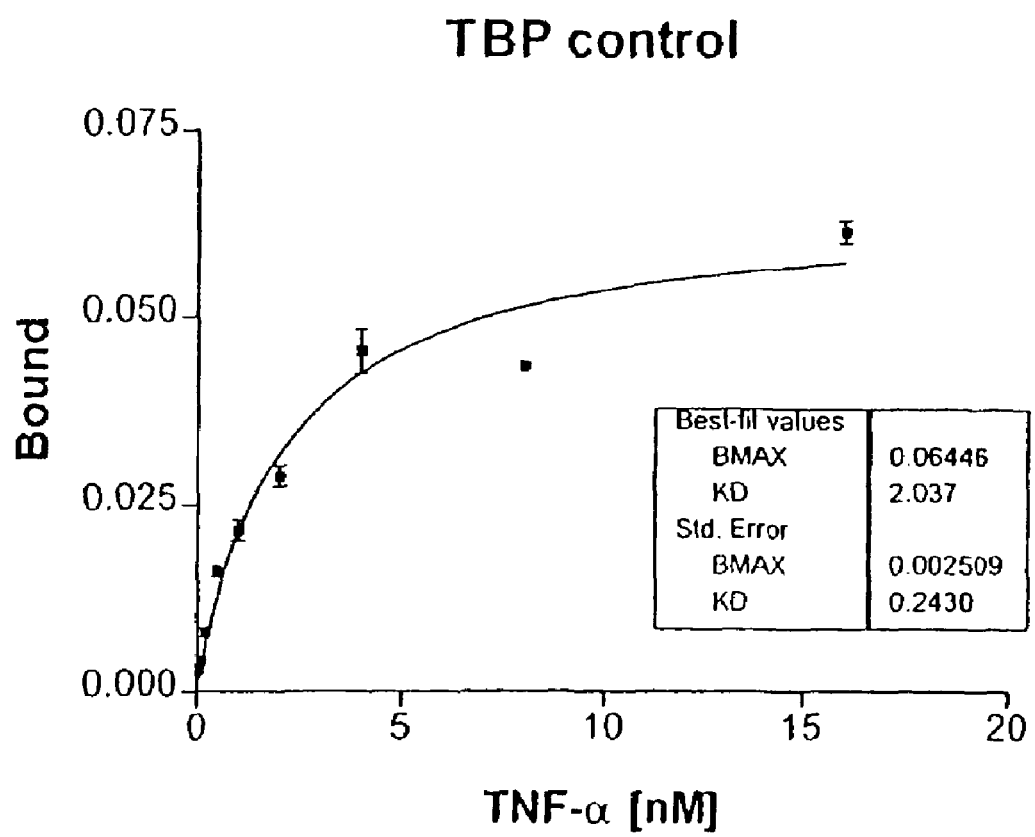
FIG. 2 is a diagrammatic representation of a saturation binding analysis of yeast expressing wild-type TNFrED (FIG. 2A), mutant clone 6 (FIG. 2B) or 11 (FIG. 2C). Triplicate samples of yeast were incubated with increasing concentrations of [$^{125}$I]TNF-α. Binding experiments were repeated two-three times with similar results.
Figure 2B:
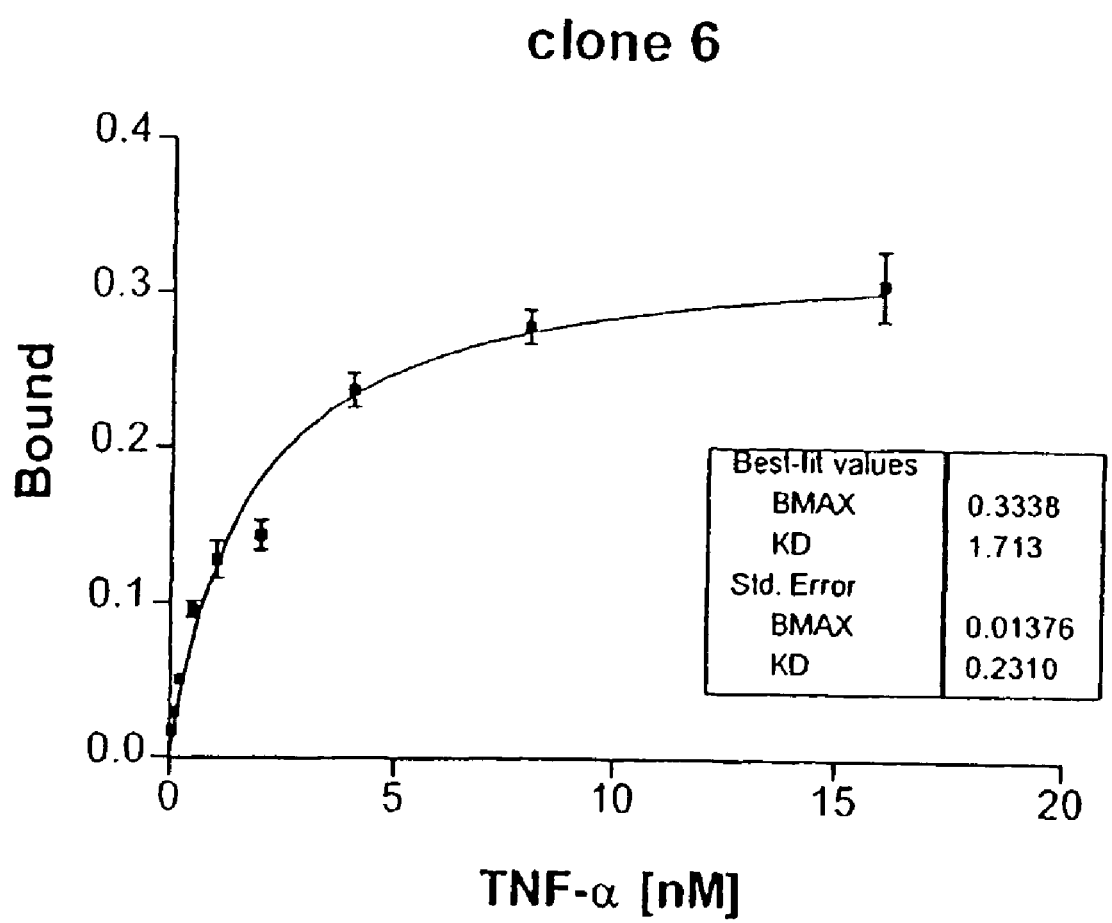
Figure 2C:
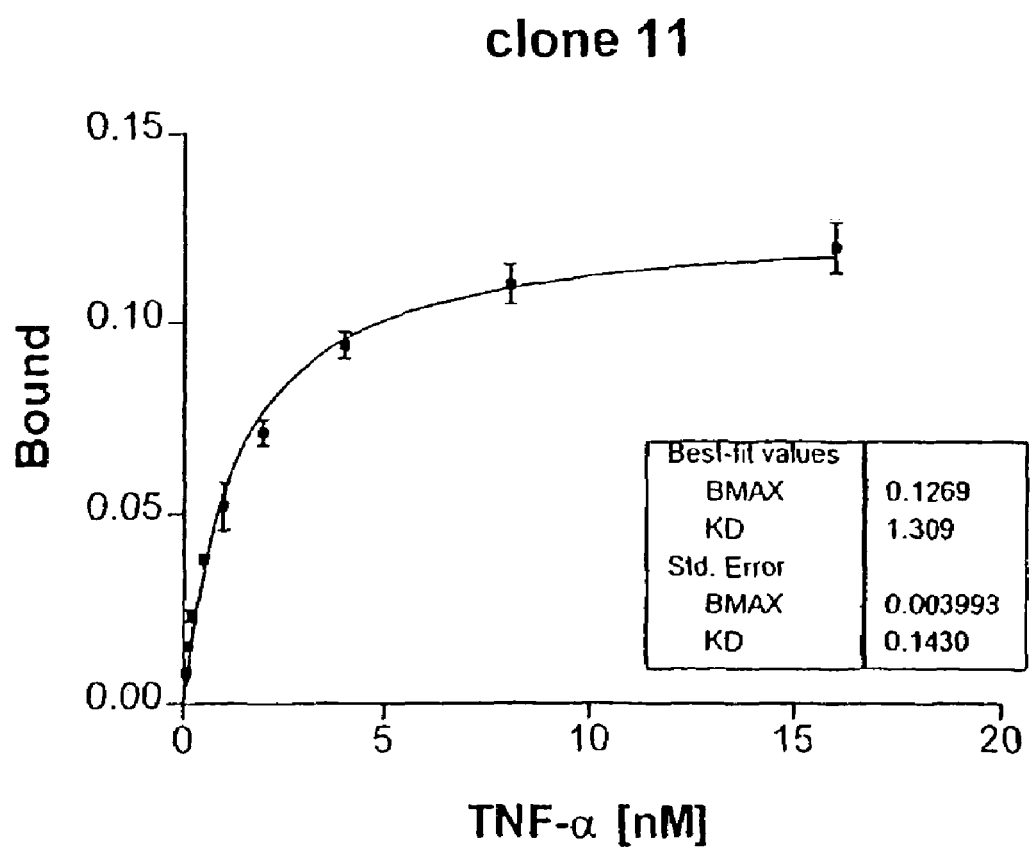

Next, it was determined whether characteristics of the mutant clones derived in yeast are similar in mammalian cells. Toward this goal we constructed a mammalian expression vector containing the human growth hormone signal sequence fused at the amino terminus to the sequence encoding mature TNFrED. We have previously found that the human growth hormone signal sequence is more efficient in inducing the secretion of TNFrED than the native signal sequence. Site-directed mutagenesis was used to incorporate each mutation found in mutant clones 6 and 11, either individually or in various combinations. The TNFrED mutants were transiently expressed in HEK293-EBNA cells and the amount of secreted TNRrED was quantitated with an ELISA specific for TNFrED. The results (Table 2) indicated that either mutation H23P or S76P increased the expression level of TNFrED. Moreover, the relative increase in expression is similar to what is seen when these mutants are expressed in yeast (FIG. 2). The S46I mutation alone did not alter the expression level of TNFrED (Table 2). The effects of these mutations do not appear to be additive as the presence of both H23P and S76P on the same construct did not increase the level of TNFrED secreted in comparison to that found with H23P alone.

The kinetics of TNF binding to the various mutants of TNFrED by surface plasmon resonance in a BIAcore instrument was also measured. The results in Table 2 indicate no difference between wild type and mutant TNFrEDs tested with respect to TNF-α binding. As indicated in Experimental Protocol, we use mild regeneration conditions and typically collect 30-40 cycles of data on every surface. We averaged results obtained on three different surfaces to obtain the means (and 95% confidence intervals) of parameters for the control. The principal error introduced by this manner of data acquisition is an increase in the variance of fitted parameters for controls when data are pooled across different surfaces and different runs (see result for purified TNFrED in Table 3). Nevertheless, the data are good enough to detect a 15% change in the $k_{on}$, a 33% change in $k_{off}$ or both. This is evidenced in the results we show for negative control and HBS (Hepes buffered saline) data collected after 27 and 36 cycles were acquired on the respective surfaces. This was done to illustrate the worst case scenario since no TNF-α binding could be measured when these "ligands" (negative control, conditioned medium, and HBS) were tested at the beginning of a run. The residue from a 36 cycle buildup of various partially denatured TNF receptor proteins demonstrates strikingly different kinetics from intact control, wild type or any mutated TNF receptor. Consistent with our findings from the yeast expression studies, the presence of H23P, S76P or S46I mutations does not alter the affinity of TNFrED for TNF-α.

TABLE 2

Transient Transfection of HEK293-EBNA cells with wild-type TNFrED and mutants of TNIFrED.

| DNA | ng/ml of TNFrED | Fold over wild-type |
|---|---|---|
| wild-type | 239 ± 5.0 | — |
| H23P | 724 ± 40 | 3 |
| S46I | 190 ± 19 | 0.8 |
| S76P | 361 ± 21 | 1.5 |
| H23P, S46I | 614 ± 54 | 2.6 |
| H23P, S76P | 711 ± 33 | 3 |
| H23P, S46I, S76P | 704 ± 26 | 2.9 |

HEK293-EBNA cells were transiently transfected with plasmid DNA. 48 h post-transfection the conditioned medium was collected and the amount of TNFrED was quantitated with an ELISA. The amount of TNFrED is the mean of four dishes±the standard deviation. This experiment was repeated three times and similar results were obtained. A single representative experiment is shown.

TABLE 3

Binding Kinetics and TNF Affinity of TNF-rED mutants.

| Sample | $K_{on}$ ×10⁶ M⁻¹s⁻¹ | $k_{off}$ ×10⁻³ s⁻¹ | $K_D$ ×10⁻⁹ M | $R_{max}$ RU | $\chi^2$ |
|---|---|---|---|---|---|
| wild-type TNFrED | 2.0 | 0.8 | 0.4 | 88.9 | 7.2 |
| H23P | 1.9 | 0.9 | 0.5 | 88.5 | 7.6 |
| S46I | 1.9 | 0.9 | 0.5 | 85.4 | 7.0 |
| S76P | 2.0 | 1.1 | 0.6 | 90.3 | 4.7 |
| H23P + S46I | 1.9 | 1.2 | 0.6 | 84.2 | 3.9 |
| H23P + S76P | 1.9 | 1.2 | 0.6 | 86 | 4.9 |
| H23P + S76P + S46I | 1.8 | 1.0 | 0.6 | 82 | 4.7 |
| negative control | 1.3 | 2.0 | 1.6 | 25.1 | 0.9 |
| HBS | 1.3 | 1.9 | 1.5 | 24.2 | 0.8 |
| purified TNFrED Avg ± 95% C.I. | 2.0 ± 0.3 | 0.9 ± 0.3 | 0.5 ± 0.1 | 77.5 ± 3 | |

Each TNFrED and control sample listed was analyzed with seven different concentrations of TNF-α (see Experimental Protocol). For a seven level data set $k_{on}$, $k_{off}$ and $R_{max}$ were fit globally using a model which incorporates baseline drift. The negative control (conditioned medium) and the HBS control show $K_d$ values of ~1.5 nM due to the mild regeneration conditions used (see Experimental Protocol). Under these conditions, we routinely note analyte-independent 0.5-1.0 RU/cycle upward movement in the absolute value of Rpoint baseline (data not shown). We suspected this result was due to small amounts of partially denatured TNFrED and mutant TNFrED remaining after each regeneration treatment and checked to see that it did not depend upon the nature of the mutant (data not shown). Analysed prior to a 27-36 cycle run of data collection, negative controls showed no TNF-α binding.

EXAMPLE 5

Examination of the Locations of Substituted Residues in Crystal Structures of TNFrED The proline substitutions in mutant clone 6 and 11 are adjacent to cysteine residues (cysteines 33 and 88) involved in disulfide bonds. To analyze whether there is a potential structural role for the mutant residues, we tabulated the conformational preferences of proline, serine, histidine and isoleucine residues in the crystal structures of TNFrED (pdb codes: 1ext, 1ncf and 1tnr) and in general protein structures. Since the conformation of polypeptides is controlled by the φ-ψ angles of the residues, we plotted the φ-ψ distribution of those residues in the dataset of high-resolution and non-homologous protein structures. As shown in FIG. 3, the φ-ψ distribution of a proline residue is more restricted than that of the other three residues, and the φ-ψ. distribution of a serine residue is greater than that of an isoleucine residue. Specifically, the size ratio of the distributions for serine to proline is 2.5, for histidine to proline is 1.8, and for serine to isoleucine is 1.4. Moreover, the φ-ψ. angles of S76 and of H23 in TNFrED crystal structures (red filled marks) preferentially overlap the favored region of proline's φ-ψ plot as compared to the favored region of φ-ψ plots for serine or histidine. This preference is slightly more noticeable in the crystal structures of TNFrED itself (pdb code: 1ext; resolution 1.85 A [red squares], or 1ncf, resolution 2.85 A [red diamonds]) than in the crystal structure of the TNF/TNFrED complex (pdb code: 1tnr; resolution 2.85 A [red triangles]). In contrast, the φ-ψ angles of Ser46 in TNFrED crystal structures are located in a slightly more favored region in the serine φ-ψ plot compared to that found with isoleucine, although the strongly favored region of either residue does not significantly overlap the distribution taken from crystal structures.

To assess the effect of adjacent residues in the choice of ϕ-ψ preferences by the substituted residue, we analyzed the ϕ-ψ angles in the pdb database representative set containing the same tri- (green 'x's) or tetra-(green circles) peptide fragments as those in clone 6, clone 11 or wild-type TNFrED. As shown in FIG. 3 and listed in Table 4, there are more cases of proline residues in which the ϕ-ψ angles are similar to those of H23 or S76 in the TNFrED crystal structures than there are of histidine or serine residues with ϕ-ψ angles similar to those of H23 or S76. The data are consistent with the ϕ-ψ angles of S46 in the TNFrED crystal structures being slightly more favored for a serine residue than for an isoleucine.

TABLE 4

List of crystal structures containing the same tri- or tetra- amino acid sequence as those in the wild-type TNFrED or mutant clones.

| Residue | Surrounding Sequence | Pdb code containing the sequence | | Similar/distinct ratio |
|---|---|---|---|---|
| | | Distinct ϕ-ψ[a] | Similar ϕ-ψ[a] | |
| Ser76 in wild-type | Ser-Ser-Cys[b] | 1arb, 1nxb, 2pia, 3ebx, 1bgc, 1frr | 1tml, 4cha | 2/6 |
| | Ile-Ser-Ser-Cys or Ser-Ser-Cys-Thr | None | None | — |
| Pro76 in clone 6 | Ser-Pro-Cys | 2tgi | 2ctc, 1tfg | 2/1 |
| | Ile-Ser-Pro-Cys or Ser-Pro-Cys-Thr | None | None | — |
| His23 in wild-type | Cys-His-Lys | 3cy3 | None | 0/1 |
| | Lys-Cys-His-Lys or Cys-His-Lys-Gly | None | None | — |
| Pro23 in clone 11 | Cys-Pro-Lys | 1tgx (2 locations) | 1tgs, 3sic, 8can | 3/2 |
| | Lys-Cys-Pro-Cys | None | 8can | 1/0 |
| | Cys-Pro-Lys-Gly | None | 1tgx | 1/0 |
| Ser46 in wild-type | Glu-Ser-Gly- | 1fha (2 locations), 1mam, 2had, 2tmd, 3gbp | 1ads, 1btc, 1fba, 1hil, 1lga, 3il8, 1nar, 1ptx, 1ttb, 4fxn, 1ovb, 2pia | 12/6 |
| | Glu-Ser-Gly-Ser | 1ovb | None | 0/1 |
| | Cys-Glu-Ser-Gly | 2pia | None | 0/1 |
| Ile46 in clone 11 | Glu-Ile-Gly | 2mnr, 2tmd, 8can | 1btl, 2ak3, 1ppb, 1xim | 4/3 |
| | Cys-Glu-*Ile*-Gly or Glu-Ile-Gly-Ser | None | None | — |

[a] The criteria for similar ϕ-ψ angles is that the ϕ-ψ angle of the subject residue is within 15 degree of the ϕ-ψ angles found in the corresponding residue of any of the TNFrED crystal structures.
[b] The residues in bold are either the substituted residue in the mutant clone or the residue found in wild-type TNFrED.

Experimental Protocols Used in the Examples

Plasmids.

The TNFrED-agglutinin fusion was constructed by linking the signal sequence from the invertase gene to the hTNFrED sequence encoding residues 12 to 172 which was then fused to the C-terminal portion of the α-agglutinin gene encoding residues 330 to 650 (1, 27). Between TNFrED and the α-agglutinin gene was a sequence encoding the flexible linker GQPAAAPA. This linker is similar to the sequence of hinges between domains in immunoglobulins. The TNFrED-agglutinin fusion gene was subcloned into the pYES2 vector (Invitrogen Corp.) to generate pYES2-TNFrED-Agg for expression in yeast.

The hTNFrED coding sequence from residue 12 to residue 172 was subcloned into pCMV, a mammalian expression vector, to generate pCMV-TNFrED. In pCMV-TNRrED the human growth hormone signal sequence is fused upstream of the hTNFrED sequence. The expression of hTNFrED in pCMV is regulated by the human cytomegalovirus (CMV) immediate-early enhancer/promoter region. Downstream of hTNFrED is the human growth hormone polyadenylation signal. pCMV-TNFrED containing either the mutation S46I or S76P was generated by subcloning the appropriate region from mutant clones 6 and 11, respectively. pCMV-TNFrED containing the H23P mutation was generated using the whole vector PCR technique (6). Combinations of the mutations of TNFrED (H23P+S46I, H23P+S76P, H23P+S46I+S76P) was accomplished by subcloning the appropriate regions. The sequence of the coding region of all constructs was verified with the Thermo Sequenase radiolabeled terminator cycle sequencing kit (Amersham Pharmacia Biotech).

Expression of TNFrED on the Surface of Yeast Cells.

*Saccharomyces cerevisiae* strain BJ2168 (a, prc1-407, prb1-1122, pep4-3, leu2, trp1, ura3-52; Yeast Genetic Stock Center, Berkeley, Calif.) was transformed with either pYES2 or pYES2-TNFrED-Agg using the lithium acetate method previously described (Gietz, R. D., Schiestl, R. H., Willems, A. R. & Woods, R. A. Studies on the transformation of intact yeast cells by the LiAc/SS-DNA/PEG procedure. *Yeast*. 11, 355-360, 1995). Transformed yeast cells were grown overnight in Ura⁻ medium supplemented with 2% glucose at 30° C. with shaking. Expression was induced by growing the transformed yeast overnight at 30° C. with shaking in Ura⁻ medium containing 2% galactose and 1% raffinose. Cells were harvested by centrifuging at 16,060×g for 2 min, washing twice with Dulbecco's phosphate-buffered saline (PBS) (Gibco/BRL) and diluting the cells to 4×10⁶ cells/ml. 4×10⁵ cells (100 ul) were incubated with either biotinylated hTNF-α (50 nM or 10 nM) or goat anti-human sTNF RI antibodies (0.7 ug/ml, R&D Systems) or both for 1 h at room temperature in a final volume of 140 ul. hTNF-α (Protein Purification group, Serono Reproductive Biology Institute) was biotinylated with the EZ-link Sulfo-NHS-LC-Biotinylation kit (Pierce Corp.). Following the incubation, cells were centrifuged at 16,060×g for 2 min and re-suspended in 140 ul of ice-cold PBS containing 0.1% bovine serum albumin (BSA). FITC-labeled avidin (2.2 ug/ml, Jackson ImmunoResearch) or R-Phycoerythrin-conjugated donkey anti-goat IgG (2.2 ug/ml, Jackson ImmunoResearch) or both were added to cells in a total volume of 180 ul and incubated at 4° C. for 45 min. Cells were centrifuged at 16,060×g for 2 min, washed once with ice-cold 1×RDF1 buffer (R&D Systems), re-suspended in ~400 ul of 1X RDF1 buffer and analyzed on Becton Dickinson FACSort. The event rate was set at approximately 150 cells/sec and a total of 10,000 cells were collected per analysis. The yeast population was gated according to light scatter (size) to avoid analysis of clumped cells.

Production and Selection of Random Mutant Libraries:

Five unique restriction endonuclease recognition sites were introduced into the coding region of TNFrED by silent mutagenesis using the GeneEditor in vitro Site-Directed Mutagenesis System (Promega Corp.). This step was completed in order to divide the TNFrED into 6 regions of between 40 to 105 bp. Five of the six regions were separately subjected to a modification of a random mutagenesis method previously described. Briefly, long oligonucleotides (Midland Certified Reagent Company) spanning a region of TNFrED flanked by unique restriction endonuclease recognition sites were generated that contain a predetermined amount of the three "wrong" phosphoramidites at each position. The amount of spiked wrong phosphoramidites was adjusted to generate an average of either two or three mutations per oligonucleotide. Primers flanking the mutated, long oligonucleotide were used in a polymerase-chain reaction to amplify the DNA into cassettes for each region of TNFrED. Randomly mutagenized DNA regions were digested with the appropriate restriction endonucleases and ligated into the pYES2-TNFrED-Agg construct. Ligation reactions for each mutant library were transformed into XL10-Gold ultracompetent cells (Stratagene Corp.) using a ratio of 1 ul of ligation mixture per 70 ul of competent cells following the manufacturer's protocol. Following the transformation, 20 transformation mixes from each mutant library were pooled and grown overnight at 37° C. in 500 ml of NZY medium containing 50 ug/ml of ampicillin. Ten random clones from each mutant library were sequenced using the Thermo Sequenase radiolabeled terminator cycle sequencing kit (Amersham Pharmacia Biotech). Approximately 5.0 ug of DNA from each random library was transformed into ten aliquots ($1\times10^9$ cells/aliquot) of BJ2168 cells using the lithium acetate transformation method. Cells were grown for 24-30 h at 30° C. with shaking. Then approximately $1\times10^8$ cells were grown overnight at 30° C. with Ura⁻ medium containing 2% galactose and 1% raffinose for the induction of expression. For each FACS experiment, $4\times10^6$ cells were labeled as described above using biotinylated hTNF-α at a final concentration of 50 nM for the mutant library containing mutant clone 6 or 10 nM for the other mutant libraries. Goat anti-human sTNF R1 antibodies were added along with FITC-avidin and R-phycoerythrin-conjugated anti-goat IgG. A total of $1.2\times10^7$ cells was sorted for each library. FACS was completed on a Becton Dickinson FACsort with an event rate of <2000 cells/sec. The first round of sorting was performed in exclusion mode and subsequent sorting was completed in single cell mode. Collected cells were seeded into selection medium with glucose and 1/100 volume was plated for calculating actual number of cells collected. Selected cells were re-grown at 30° C. and then induced in selection medium with galactose and raffinose for the next round of sorting. Each library was sorted a total of three to four times. Approximately 0.08%-0.4% of cells were collected in the first round, and 0.01%-0.2% in the subsequent rounds. The collected cells from the last round of sorting were plated Ura⁻ plates to yield single colonies.

Recovery and Analysis of Mutant TNFrED Clones:

Approximately 50 individual yeast clones from each library sort were analyzed by flow cytometry. 100 ul of induced cells at 0.15 $OD_{600nm}$ were incubated with either 50 nM or 10 nM biotinylated TNF-α in a total volume of 140 ul, under same conditions as described above. Binding of TNF-α was detected with FITC-avidin (2.2 ug/ml), and cells were analyzed by flow cytometry on the Becton Dickinson FACsort. Clones having a greater median fluorescence than yeast expressing pYES2hTNFrED-Agg control were chosen for rescue of plasmid. DNA plasmids were recovered from yeast, and transformed into competent E. Coli JM109 (Promega Corp.) following the manufacturer's protocol. Purified plasmid DNA was re-transformed into BJ2168 yeast cells as described above and individual clones were re-analyzed using methods described above. The TNFrED regions of positive clones after the re-transformation were sequenced using the Thermo Sequenase radiolabeled terminator cycle sequencing kit (Amersham Pharmacia Biotech).

TNF-αBinding Assay

Yeast expressing either the wild-type or mutant TNFrED-agglutinin fusion or yeast containing the control vector pYES2 were resuspended in PBS/BSA (10 mg/ml) at a concentration of $1\times10^8$ cells/ml. In each well of a Durapore 96-multi-well plate (Millipore Corp.), 50 ul of the cell suspension were incubated with 50 ul of PBS/B SA (10 mg/ml) containing various concentrations of $^{125}$I-TNF-α (Amersham Pharmacia Biotech) for 2 h at room temperature. Following the incubation, the wells were washed three times with ice-cold PBS using the MultiScreen filtration system (Millipore Corp.). Non-specific binding was determined with the yeast containing the control vector pYES2 and the non-specific binding was <10% of the total counts. The Kd and Bmax was determined using the GraphPad Prism program.

Expression of TNFrED Mutants.

The pCMVhTNFrED constructs were transiently transfected into HEK293-EBNA cells using a calcium phosphate method. Transfections were completed in triplicate and hTNFrED expression was quantitated from medium harvested 48 h post-transfection using an ELISA for hTNF R-1 (R & D Systems).

BIAcore Analysis of TNFrED mutants.

Surfaces displaying polyclonal goat anti-human TNFrED were constructed by binding biotinylated antibody (BAF225 from R&D Systems) to streptavidin-coated Sensor SA chips (P/N BR-1000-32, BIAcore Inc.). Under the conditions of these experiments the streptavidin-biotinylated anti-TNFrED interaction behaves as if irreversible. Data for the comparison of TNFrED/TNF-α interaction between mutants and wild-type TNFrED were collected in HBS (10 mM HEPES pH 7.4, 150 mM NaCl, 3.4 mM EDTA, 0.005% P20) as follows.

Conditioned media from transient transfections of HEK293-EBNA cells were concentrated with Centricon 10s and the amount of TNFrED protein was quantitated with the R & D Systems ELISA for hTNF R-1. Buffer-diluted purified TNFrED (BS03-99, obtained from IRCS) or buffer-diluted conditioned medium containing a mutated protein was injected onto a BAF225 surface at 50 nM, resulting in the formation of antibody-TNFrED complex. TNF-α at 1 nM (trimer in HBS) was then injected, and kinetics of the binding and dissociation were recorded via the time course of the surface plasmon resonance response. The BAF-225 surface was regenerated with 50% 100 mM sodium citrate pH 2.5/50% 100 mM sodium citrate pH 3., which stripped off TNFrED and TNF-α. This series of injections was repeated for TNF-α at 2, 5, 10, 20, 50, and 100 nM while holding the concentration of TNFrED injected (wild-type or mutant) at 50 nM. Each set of binding curves was fit globally using a model for 1:1 interaction that includes a term for linear baseline drift. Conditioned medium (no TNFrED) and HBS were used as negative controls. The BAF225 surface was regenerated with 50% 100 mM sodium citrate pH 2.5/50% 100 mM sodium citrate pH 3., which stripped off TNFrED and TNF-α. In our hands it has been necessary to have fairly mild regeneration conditions to achieve a data collection rate sufficiently high to make this technology useful.

Analysis of Crystal Structures.

A dataset previously described (Wang, Y., Huq, H. I., de, 1. C., X & Lee, B. A new procedure for constructing peptides into a given Calpha chain. Fold. Des. 3, 1-10, 1998) was used to analyze the φ-ψ angle distributions of proline, serine, histidine and isoleucine residues in high-resolution and non-homologous protein crystal structures. This dataset contains 136 x-ray structures with a resolution of 1.8 angstroms or higher, and with the sequence identity of less than 25% between any pair in the set. There are 803 proline, 1251 serine, 409 histidine and 959 isoleucine residues in the dataset. The φ-ψ angle space is equally divided into 36×36 bins with an interval of 10 degree from −180 degree to 180 degree for φ or ψ angle. The darkness of a bin in the φ-ψ angle distribution diagrams (FIG. 3) is associated with the frequency of binomial distribution of the amino acid residue in the dataset. The higher the frequency, the darker the bin. The lightest gray bins represent a dimensionless ratio of Z value (fold of probable error over the basal probability) of 1. The Z value of the darkest (black) bins is 40 or above, and that of other grey bins is 3, 5, 10 and 30, respectively. The basal probability is np, where n is the total number of the amino acid residue in the dataset and the p is 1/(36×36), and the error variance σ is:

$$\sqrt{np(1-p)}$$

Both the above dataset and the Hobohm's dataset (Hobohm, U. & Sander, C. Enlarged representative set of protein structures. *Protein Sci.* 3, 522-524, 1994) were used to search for a tri- or a tetra-amino acid sequence corresponding to the same sequence surrounding either the mutated residues or the wild-type sequence. The reason to include the Hobohm's dataset for the search is to increase the number of protein structures containing the sequence to increase the statistical relevance. There are 168 protein structures in the Hobohm dataset, and 35 structures are in overlap with the first dataset. The combined dataset contains 269 non-redundant protein structures, which represents the different type of folds and sequences of the whole PDB database. The pdb codes of the three crystal structures containing TNFrED molecules are 1ext, 1ncf and 1tnr. These structures are not in any of the above datasets.

The invention has been described in detail with reference to preferred embodiments thereof. However, it will be appreciated that those skilled in the art, upon consideration of this disclosure, may make modifications and improvements within the spirit and scope of the invention.

REFERENCE LIST

1. Edgington, S. M. Rites of passage: moving biotech proteins through the ER. *Biotechnology* (N.Y.) 10, 1413-1420 (1992).
2. Eyles, S. J. & Gierasch, L. M. Multiple roles of prolyl residues in structure and folding. *J. Mol. Biol.* 2000. Aug. 18.;301. (3.). 737.-47.301, 737-747 (2000).
3. Tuite, M. F. & Freedman, R. B. Improving secretion of recombinant proteins from yeast and mammalian cells: rational or empirical design? *Trends. Biotechnol.* 12, 432-434 (1994).
4. Wittrup, K. D. Disulfide bond formation and eukaryotic secretory productivity. *Curr. Opin. Biotechnol.* 6, 203-208 (1995).
5. Boder, E. T. & Wittrup, K. D. Yeast surface display for screening combinatorial polypeptide libraries. *Nat. Biotechnol.* 15, 553-557 (1997).
6. Boder, E. T., Midelfort, K. S. & Wittrup, K. D. Directed evolution of antibody fragments with monovalent femtomolar antigen-binding affinity. *Proc. Natl. Acad. Sci. U.S.A.* 2000. Sep. 26.;97. (20.):10701. -5. 97, 10701-10705 (2000).
7. Holler, P. D. et al. In vitro evolution of a T cell receptor with high affinity for peptide/MHC. *Proc. Natl. Acad. Sci. U.S.A.* 2000. May. 9. ;97. (10.):5387.-92. 97,5387-5392 (2000).
8. Kieke, M. C., Cho, B. K., Boder, E. T., Kranz, D. M. & Wittrup, K. D. Isolation of anti-T cell receptor scFv mutants by yeast surface display. *Protein Eng.* 10, 1303-1310 (1997).
9. Kieke, M. C. et al. Selection of functional T cell receptor mutants from a yeast surface-display library. *Proc. Natl. Acad. Sci. U.S.A.* 96, 5651-5656 (1999).
10. Shusta, E. V., Kieke, M. C., Parke, E., Kranz, D. M. & Wittrup, K. D. Yeast polypeptide fusion surface display levels predict thermal stability and soluble secretion efficiency. *J. Mol. Biol.* 292, 949-956 (1999).
11. Hamilton, K. & Clair, E. W. Tumour necrosis factor-alpha blockade: a new era for effective management of rheumatoid arthritis. *Expert. Opin. Pharmacother.* 2000. Jul. 1. (5.):1041.-52. 1, 1041-1052 (2000).
12. Kam, L. Y. & Targan, S. R. TNF-alpha antagonists for the treatment of Crohn's disease. *Expert. Opin. Pharmacother.* 2000. May. ;1. (4.).615. -22. 1, 615-622 (2000).
13. Schreuder, M. P., Brekelmans, S., van den Ende, H. & Klis, F. M. Targeting of a heterologous protein to the cell wall of *Saccharomyces cerevisiae*. *Yeast.* 9, 399-409 (1993).
14. Schreuder, M. P., Mooren, A. T., Toschka, H. Y., Verrips, C. T. & Klis, F. M. Immobilizing proteins on the surface of yeast cells. *Trends. Biotechnol.* 14, 115-120 (1996).
15. Hermes, J. D., Parekh, S. M., Blacklow, S. C., Koster, H. & Knowles, J. R. A reliable method for random mutagenesis: the generation of mutant libraries using spiked oligodeoxyribonucleotide primers. *Gene* 84, 143-151 (1989).
16. Naismith, J. H., Devine, T. Q., Kohno, T. & Sprang, S. R. Structures of the extracellular domain of the type I tumor necrosis factor receptor. *Structure.* 4, 1251-1262 (1996).
17. Naismith, J. H., Devine, T. Q., Brandhuber, B. J. & Sprang, S. R. Crystallographic evidence for dimerization of unliganded tumor necrosis factor receptor. *J. Biol. Chem.* 270, 13303-13307 (1995).
18. Banner, D. W. et al. Crystal structure of the soluble human 55 kd TNF receptor-human TNF beta complex: implications for TNF receptor activation. *Cell* 73, 431-445 (1993).
19. Wang, Y., Huq, H. I., de, l. C., X & Lee, B. A new procedure for constructing peptides into a given Calpha chain. *Fold. Des.* 3, 1-10 (1998).
20. Bazzoni, F. & Beutler, B. The tumor necrosis factor ligand and receptor families. *N. Engl. J. Med.* 334, 1717-1725 (1996).
21. Gietz, R. D., Schiestl, R. H., Willems, A. R. & Woods, R. A. Studies on the transformation of intact yeast cells by the LiAc/SS-DNA/PEG procedure. *Yeast.* 11, 355-360 (1995).
22. Robzyk, K. & Kassir, Y. A simple and highly efficient procedure for rescuing autonomous plasmids from yeast. *Nucleic. Acids. Res.* 20, 3790 (1992).
23. Jordan, M., Schallhom, A. & Wurm, F. M. Transfecting mammalian cells: optimization of critical parameters affecting calcium-phosphate precipitate formation. *Nucleic. Acids. Res.* 24, 596-601 (1996).
24. Hobohm, U. & Sander, C. Enlarged representative set of protein structures. *Protein Sci.* 3, 522-524 (1994).

The invention claimed is:

1. An isolated mutant of a native polypeptide wherein the native polypeptide comprises the amino acid sequence of SEQ ID NO: 1, and wherein the amino acid at position 23 or the amino acid at position 76 of SEQ ID NO: 1 is substituted with proline and wherein said mutant exhibits increased expression compared with that of the native polypeptide.

2. The polypeptide of claim 1, wherein the amino acid at position 23 of SEQ ID NO: 1 is substituted with proline.

3. The polypeptide of claim 1, wherein the amino acid at position 76 of SEQ ID NO: 1 is substituted with proline.

4. A method of producing an isolated mutant of a native polypeptide comprising:

a. providing an in vitro host cell comprising an isolated nucleic acid encoding the polypeptide of claim 1, 2 or 3; and b. expressing the mutant polypeptide; and optionally c. recovering the mutant polypeptide.

5. A method of producing an isolated mutant of a native polypeptide comprising:

a. providing an in vitro host cell comprising an expression vector comprising an isolated nucleic acid encoding the polypeptide of claim 1, 2 or 3; and b. expressing the mutant polypeptide; and optionally c. recovering the mutant polypeptide.

* * * * *

SEQUENCE LISTING

<160> NUMBER OF SEQ ID NOS: 3

<210> SEQ ID NO 1
<211> LENGTH: 161
<212> TYPE: PRT
<213> ORGANISM: Homo sapiens

<400> SEQUENCE: 1

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn

<210> SEQ ID NO 2
<211> LENGTH: 486
<212> TYPE: DNA
<213> ORGANISM: Homo sapiens

<400> SEQUENCE: 2
gatagtgtgt gtccccaagg aaaatatatc caccctcaaa ataattcgat ttgctgtacc      60
aagtgccaca aggaaccta cttgtacaat gactgtccag gcccggggca ggatacggac     120
tgcagggagt gtgagagcgg atccttcact gcttcagaaa accacctcag acactgcctc     180
agctgctcca aatgccgaaa ggaaatgggt caggtggaga tctcttcttg cacagtcgac     240
cgggacaccg tgtgtggctg caggaagaac cagtaccggc attattggag tgaaaacctt     300
ttccagtgct tcaattgcag cctctgcctc aatgggaccg tgcacctctc ctgccaggag     360
aaacagaaca ccgtgtgcac ctgccatgca ggtttctttc taagagaaaa cgagtgtgtc     420
tcctgtagta actgtaagaa aagcctggag tgcacgaagt tgtgcctacc ccagattgag     480
aattga                                                                486

<210> SEQ ID NO 3
<211> LENGTH: 486
<212> TYPE: DNA
<213> ORGANISM: Homo sapiens

<400> SEQUENCE: 3
ctatcacaca caggggttcc ttttatatag gtgggagttt tattaagcta aacgacatgg      60

-continued

```
ttcacggtgt ttccttggat gaacatgtta ctgacaggtc cgggccccgt cctatgcctg      120
acgtccctca cactctcgcc taggaagtga cgaagtcttt tggtggagtc tgtgacggag      180
tcgacgaggt ttacggcttt cctttaccca gtccacctct agagaagaac gtgtcagctg      240
gccctgtggc acacaccgac gtccttcttg gtcatggccg taataacctc acttttggaa      300
aaggtcacga agttaacgtc ggagacggag ttaccctggc acgtggagag gacggtcctc      360
tttgtcttgt ggcacacgtg gacggtacgt ccaaagaaag attctctttt gctcacacag      420
aggacatcat tgacattctt ttcggacctc acgtgcttca acacggatgg ggtctaactc      480
ttaact                                                                 486
```